United States Patent [19]

Gaucher

[11] Patent Number: 4,673,289

[45] Date of Patent: Jun. 16, 1987

[54] OPTICAL DEVICE WITH A HIGH COLLECTION EFFICIENCY AND CYTOFLUORIMETER MAKING USE OF THE SAME

[75] Inventor: Jean-Claude Gaucher, le Val St. Gerwain, France

[73] Assignee: Commissariat a l'Energie Atomique, Paris, France

[21] Appl. No.: 745,589

[22] Filed: Jun. 17, 1985

[30] Foreign Application Priority Data

Jun. 20, 1984 [FR]  France ................... 84 09676

[51] Int. Cl.⁴ .................. G01N 21/05; G01N 21/64
[52] U.S. Cl. ................... 356/72; 250/461.2; 250/573; 350/416; 356/246; 356/318
[58] Field of Search ............ 250/461.1, 461.2, 573, 250/574, 575; 356/39, 72, 73, 246, 317, 318, 335, 336, 337, 338, 343, 410, 411; 350/416

[56] References Cited

U.S. PATENT DOCUMENTS

| | | | |
|---|---|---|---|
| 3,788,744 | 1/1974 | Friedman et al. | 356/39 |
| 3,989,381 | 11/1976 | Fulwyler | 356/338 |
| 4,336,029 | 6/1982 | Natale | 250/461.2 |
| 4,348,107 | 9/1982 | Leif | 356/317 |
| 4,500,641 | 2/1985 | van den Engh et al. | 356/318 |
| 4,584,604 | 4/1986 | Guichard et al. | 358/92 |

FOREIGN PATENT DOCUMENTS

| | | | |
|---|---|---|---|
| 0068404 | 1/1983 | European Pat. Off. | 356/246 |
| 2831926 | 2/1980 | Fed. Rep. of Germany . | |

OTHER PUBLICATIONS

Tyrer, *IEEE Potentials*, Dec. 1984, p. 20.

*Primary Examiner*—F. L. Evans
*Attorney, Agent, or Firm*—James E. Nilles

[57] ABSTRACT

Optical device with a high collection efficiency and cytofluorimeter using the same. This device permits the light excitation of a flow of material directed along an axis and able to emit light when it receives it and/or collects the light emitted by said flow. It comprises a first optical element and a spherical analysis chamber which can be penetrated by the flow, defined by the element and allowing a center of symmetry. The element has a convex spherical dioptre allowing an axis of symmetry passing through the center of the chamber and said element is positioned in such a way that the axis of the flow passes through the center of the chamber. Application to the analysis of a flow of biological cells.

16 Claims, 8 Drawing Figures

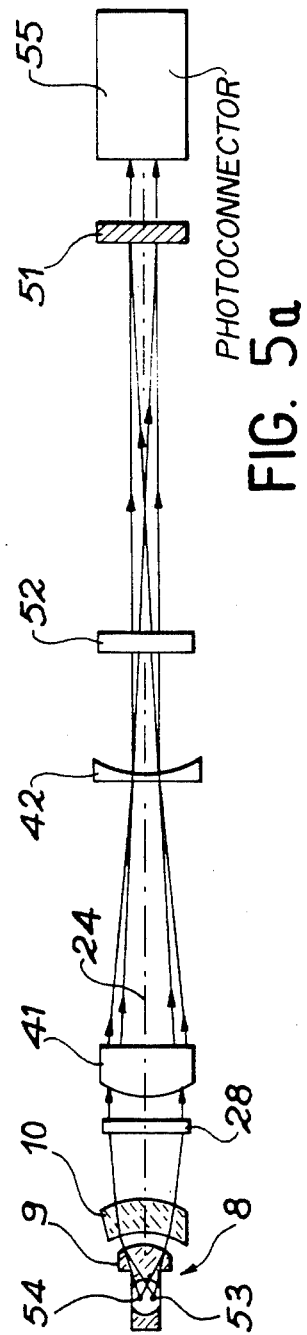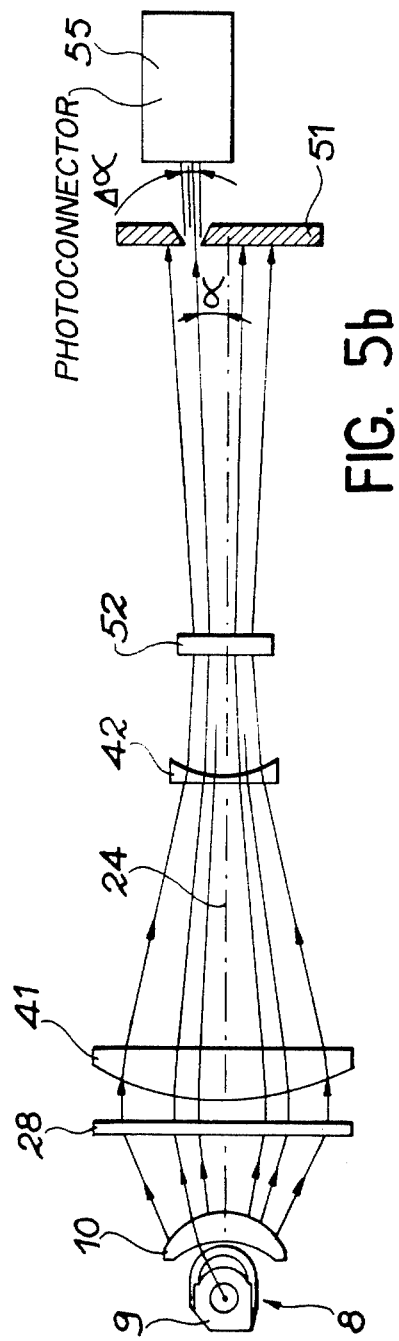
FIG. 5a
FIG. 5b

OPTICAL DEVICE WITH A HIGH COLLECTION EFFICIENCY AND CYTOFLUORIMETER MAKING USE OF THE SAME

BACKGROUND OF THE INVENTION

The present invention relates to an optical device with a high collection efficiency and to a cytofluorimeter using said device. It is more particularly used in the analysis of a flow or flux of biological cells.

Cytofluorimeters are known in which the light emitted by a flow of biological cells, illuminated by a laser, is collected by a microscope objective located at a considerable distance from the flow of cells being investigated and which has a small aperture, so that it only collects a small amount of light coming from the cells.

SUMMARY OF THE INVENTION

The object of the present invention is to obviate this disadvantage by proposing an optical device for the optical analysis of a flow of material, e.g. a flow of biological cells and which has a high collection efficiency whilst permitting, in an advantageous constructional form, to re-form the image of the illuminated point of the material flow.

The present invention more specifically relates to an optical device permitting the luminous excitation of a flow of material to be analyzed directed along an axis and able to emit light when it receives it and/or collect light emitted by the said flux, said device comprising a first optical element, wherein the device also comprises a spherical analysis chamber, which can be penetrated by the material flow, defined by the first optical element and allowing a symmetry centre, wherein the first optical element has a convex spherical dioptre allowing an axis of symmetry passing through the centre of the chamber and wherein the first optical element is positioned in such a way that the axis of the material flow passes through the centre of the chamber.

Obviously, the first optical element has another dioptre constituted by at least part of the wall of the aforementioned chamber, in such a way that the light penetrating the first element by said other dioptre can leave the same by the convex spherical dioptre, then serving as an output dioptre and vice versa.

The expression "emit light" must be understood in a general sense and not only means "producing light" under the impact of a light beam "e.g. fluorescent light of appropriate marked biological cells", but also transmit and diffract light.

The optical device according to the invention surrounds the studied flow and is very close to the latter, whilst having a large aperture as a result of the spherical dioptre equipping the same. All this provides the optical device according to the invention with a high collection efficiency.

Preferably, the analysis chamber has an optically reflecting wall positioned opposite to the dioptre with respect to the center of the chamber. This leads to a further increase in the collection efficiency of the device.

Preferably, the device according to the invention also comprises a second optical element defined by respectively concave and convex first and second spherical dioptres, allowing a common symmetry axis and positioned in such a way that its first dioptre faces the dioptre of the first optical element and the common symmetry axis coincides with the symmetry axis of the dioptre of the first optical element.

According to a preferred embodiment of the device according to the invention, the first Weierstrass point of the dioptre of the first optical element coincides with the centre of the analysis chamber and the second Weierstrass point of this dioptre constitutes both the centre of the first dioptre of the second optical element and the first Weierstrass point of the second dioptre of said second optical element.

Thus, it is possible to obtain freedom from any spherical aberrations. The aperture of the emergent beam of this assembly of two optical elements is relatively small, which makes it possible to use a conventional lens, positioned at the end of the second element, so that with minimum spherical aberration, it is possible to obtain a parallel light beam from the light coming from the second element.

According to an advantageous embodiment of the device according to the invention, the latter also comprises a collective lens placed facing the second dioptre of the second optical element, whose optical axis coincides with the symmetry axis of said second dioptre and which serves to form a parallel light beam from the light which it collects from said second dioptre.

It is then merely necessary to have a simple optical means placed at the end of said lens to reform the image of the illuminated point of the material flow studied.

The present invention also relates to a cytofluorimeter comprising means for forming a flow of biological cells directed along an axis, means for forming at least one light beam for exciting these cells, an optical device permitting said excitation and the collection of the light emitted by the flow of cells and means for analysing said light, the optical device being in accordance with the optical device according to the invention, the flow of material being the flow of cells and the first optical element being traversable by said flow of cells.

According to a special embodiment of the cytofluorimeter according to the invention, the outer face of the first optical element has at least one flat for the entry of the exciting light beam.

According to another special embodiment, the cytofluorimeter according to the invention also comprises a light reflector for collecting part of the light scattered by the flow of cells and the light of the exciting beam remaining after said excitation on leaving the optical device and for forming a parallel light beam from said remaining light, said part of the diffused light.

According to a preferred embodiment of the cytofluorimeter according to the invention, the optical device equipping the same has the aforementioned collective lens, whilst the cytofluorimeter also has an optical assembly for transforming the parallel light beam formed by the collective lens into a convergent light beam.

According to another special embodiment of the cytofluorimeter according to the invention, the axis of the flow of cells is perpendicular to the axis of symmetry of the dioptre of the first element, the exciting light beam is a laser beam striking the flow of cells at a point separate from the centre of the chamber, the optical device of the cytofluorimeter comprises the optically reflecting wall and the aforementioned collective lens, whilst the cytofluorimeter also comprises a cylindrical lens following the optical assembly and able to form two parallel light layers from the ligth emerging from said assembly, at least one analysis slit for said layers, displaceable transversely thereto and positioned following the cylindrical lens and photodetector means positioned after the analysis slit.

It is therefore possible to investigate the light diffused by the cells in accordance with large angles.

Following the optical assembly, it is optionally possible to provide a dichroic mirror which only reflects light of the same wavelength as that of the exciting light beam and which only transmits wavelengths corresponding to the fluorescenses and it is possible to position in the path of the light reflected by the dichroic mirror a cylindrical lens followed by an analysis slit, which is itself followed by the photodetector means, so that it is possible to simultaneously study the diffusion at large angles and/or the fluorescene or fluorescences.

According to another special embodiment, the axis of the flow of cells is perependicular to the symmetry axis of the dioptre of the first element, the excitation of the cells being carried out with the aid of a first and a second laser beam striking the flow of cells respectively in the centre of the analysis chamber and at a point separate from said centre and the optical device of the cytofluorimeter is provided with a reflecting wall and the collective lens referred to hereinbefore.

According to another embodiment, the cytofluorimeter according to the invention also comprises a first lens defined by a planar face and by a convex spherical dioptre, the planar face being placed against a flat of the first optical element, a second lens defined by a convex spherical dioptre and by a concave spherical dioptre facing the convex dioptre of the first lens and a telescope for transforming the excitation beam into a convergent beam with a large diameter and covering at best the convex dioptre of the second lens, wherein the first Weierstrass point of the dioptre of the first lens coincides with the centre of the analysis chamber and wherein the second Weierstrass point of this dioptre constitutes both the centre of the concave dioptre of the second lens and the first Weierstrass point of the convex dioptre of said second lens.

This special embodiment makes it possible to perform "profile measurements", i.e. study the cells in portionwise manner.

According to a special embodiment of the invention, the means for forming the excitation beam are provided for injecting the latter into the optical device in such a way that the exciting beam strikes the dioptre of the first optical element of the said optical device.

Finally, in another special embodiment, the cytofluorimeter according to the invention also comprises means for electrically analysing the cells, so that said cytofluorimeter is compatible with measurements of the COULTER type.

BRIEF DESCRIPTION OF THE DRAWINGS

The invention is described in greater detail hereinafter relative to non-limitative embodiments and the attached drawings, wherein show:

FIGS. 5a and 5b respectively side and plan diagrammatic views of means placed following the optical assembly and making it possible to study the light diffused by the cells according to large angles.

DETAILED DESCRIPTION OF THE PREFERRED EMBODIMENTS

Figure 1:
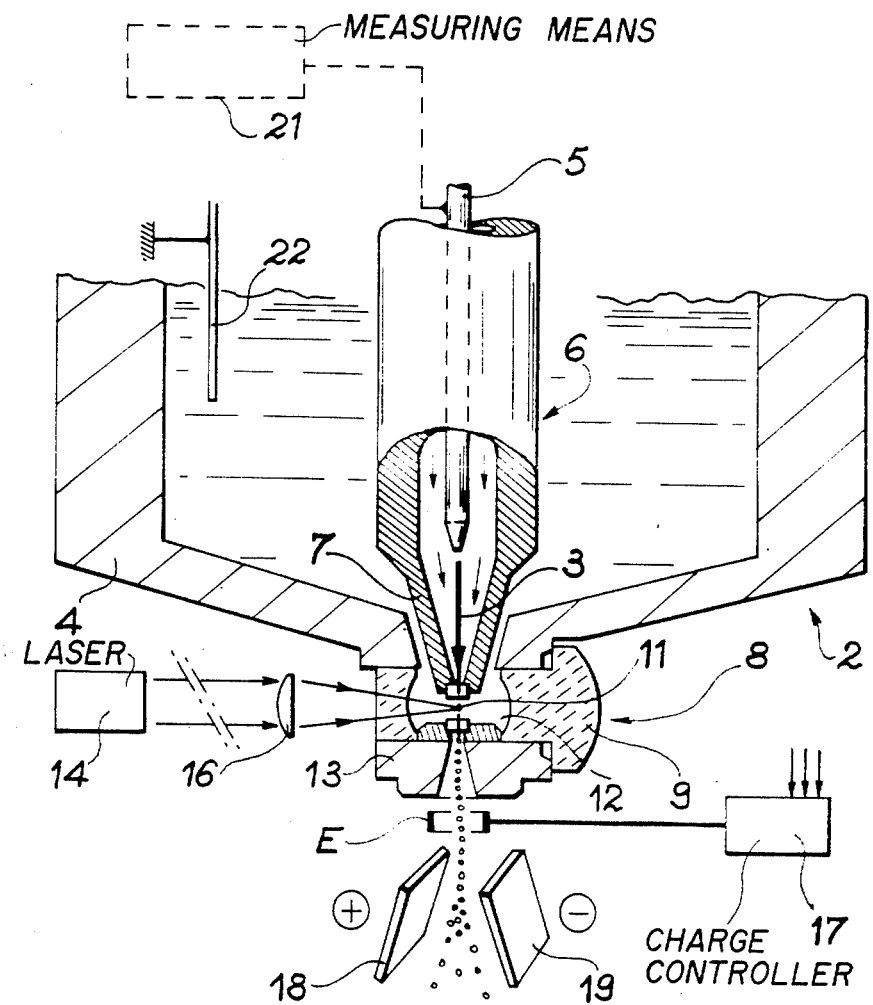
FIG. 1 a diagrammatic view of a special embodiment of the cytofluorimeter according to the invention, equipped with the optical device according to the invention.

FIG. 1 diagrammatically shows a special embodiment of the cytofluorimeter according to the invention. Thus, it comprises means 2 for forming an axial flow of biological cells 3. These means 2 comprise, in a support 4, a tube 5 for circulating a suspension of biological cells and an outflow chamber 6 containing an entraining liquid and which is terminated by a nozzle 7 making it possible to form the flow of cells.

Figure 2:
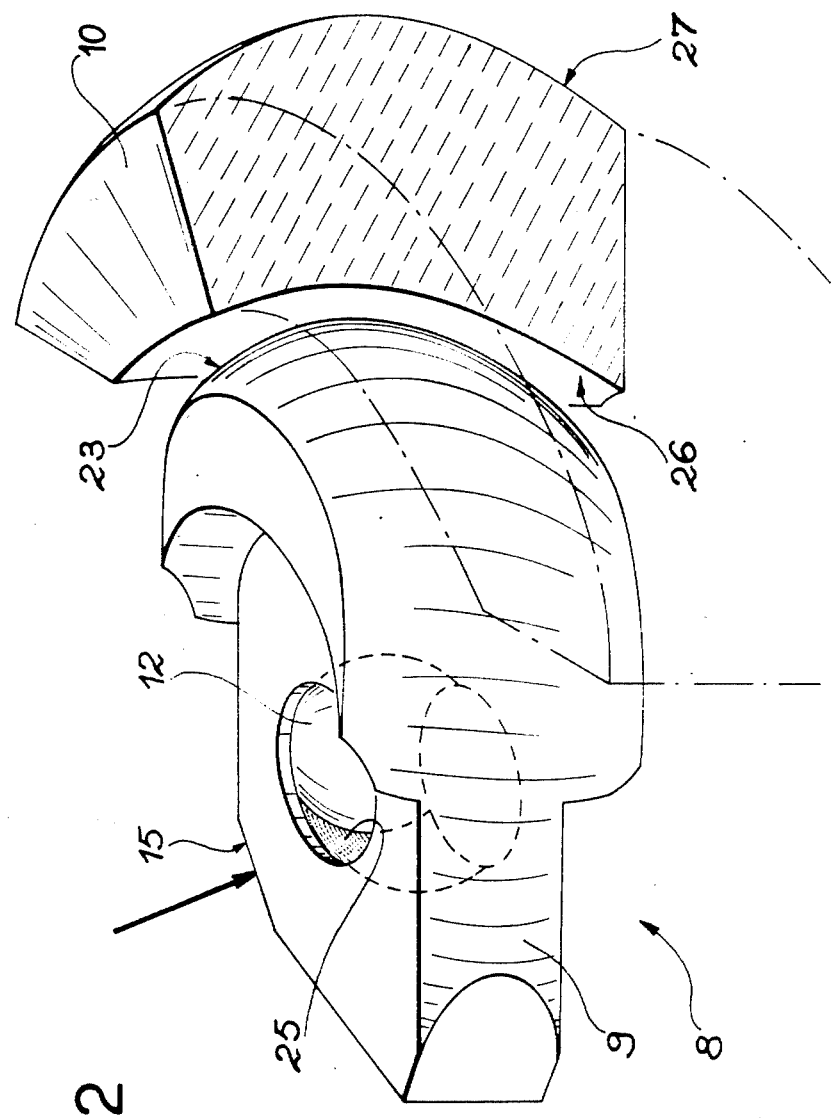
FIG. 2 a diagrammatic perspective view of the optical device.
Figure 3:
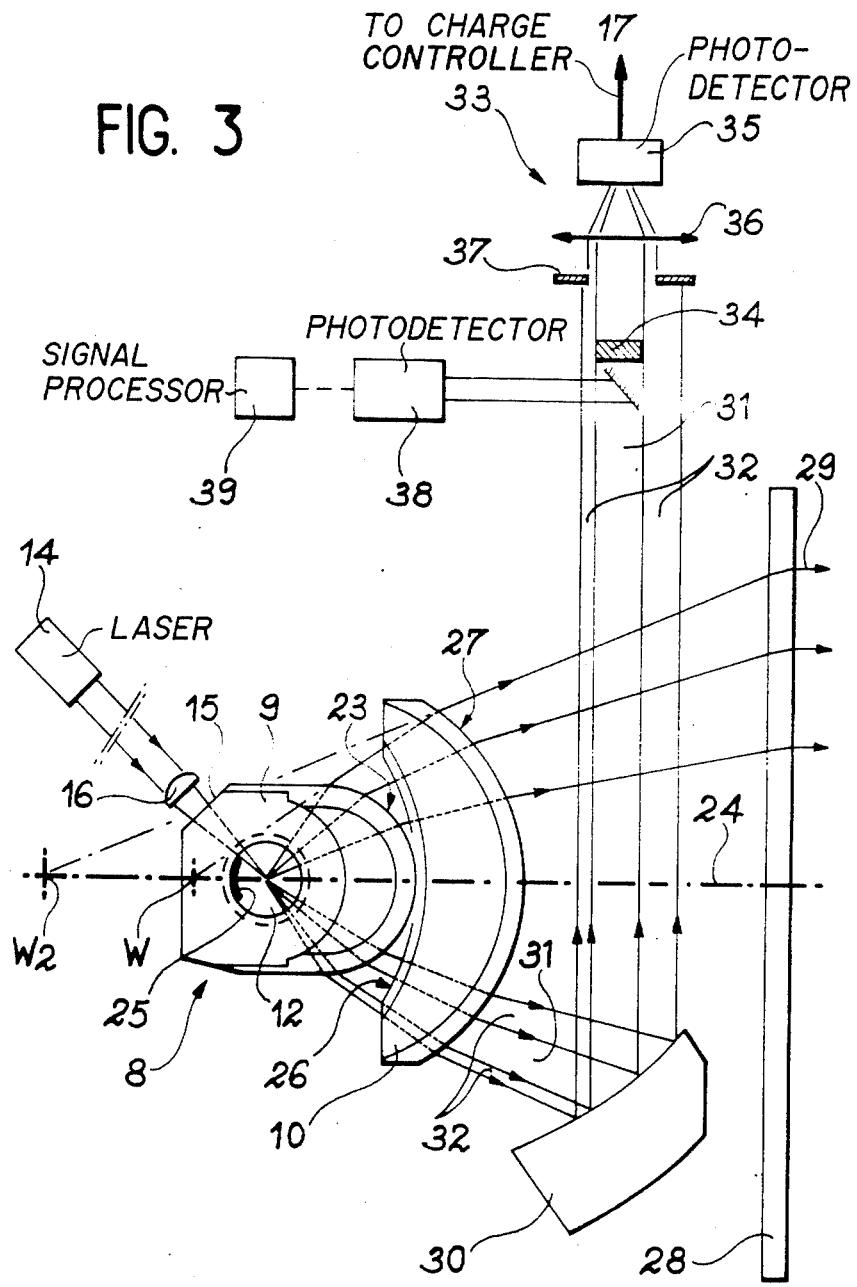
FIG. 3 a diagrammatic sectional view of said device and complementary optical means of the cytofluorimeter.

The cytofluorimeter also comprises an optical device 8 formed from a first element 9 and a second element 10 (FIGS. 2 and 3) preferably made from a material such as molten silica or the material marketed under the trade name SUPRASIL, so that these elements can be inter alia traversed by ultraviolet light used for the light excitation of the cells. The first optical element 9 is internally provided with a spherical chamber 12, whose centre is designated 11. This chamber is open at two diametrically opposite ends. The first optical element 9 is fixed to support 4, in such a way that nozzle 7 issues into the chamber by one of the ends thereof and the flow of cells formed passes through the centre of the chamber. Another nozzle 13 is fixed to the first optical element 9, so as to communicate with chamber 12 by the other end thereof and is located facing nozzle 7. The flow of cells formed, after traversing chamber 12, in this way issues into the open air via the other nozzle 13.

The cytofluorimeter also has a laser 14 able to emit a light beam, which is focused on the flow of cells, in the centre 11 of the chamber, which it penetrates by a flat 15 (FIG. 3) made on the outer face of the first optical element, a focusing lens 16 being positioned facing the flat on the path of the laser beam.

When it passes into the open air, the flow of cells is broken down into droplets by known, not shown means. The cytofluorimeter also has electronic means 17 for controlling the charge of the droplets and the sign of this charge via an annular electrode E placed in the open air, facing the other nozzle 13, in such a way that it can be traversed by the droplets, and as a function of the signals received from the difference photodetector means serving to detect the fluorescence light emitted by the appropriately marked cells, under the impact of the laser beam.

A pair of conductive plates 18, 19, respectively raised to a high positive voltage and a high negative voltage and positioned on either side of the cell flow, when the latter issues into the open air, thus make it possible to selectively pass the electrically charged droplets into containers 20.

The cytofluorimeter shown in FIG. 1 is compatible with electrical measurements of the COULTER type. Thus, it is possible to electrically count the number of cells and electrically measure the volume thereof with the aid of electronic measuring means 21 connected to tube 5, as well as an electrode 22 connected to earth and placed in the volume defined by support 4, said volume and the chamber 12 with which it communicates then being filled with a physiological liquid.

The first optical element 9 (FIGS. 2 and 3) is externally defined by a convex spherical dioptre 23, which gives it the shape of a hemisphere. The latter is located on onse side of a diametral plane of chamber 12 incorporating the axis of the flow of cells, whilst flat 15 is located on the other side of this plane. Moreover, in order to be able to insert the optical device into the cytofluorimeter, the hemisphere is defined on the side of the faces of the first optical element 9 on which issue the openings of chamber 12, by two planar faces. Dioptre 23 has an axis of symmetry 24 constituting the optical axis of optical device 8 and which passes through the centre 11 of chamber 12, whilst being perpendicular to the axis of the flow of cells.

The light transmitted, scattered and possibly produced by the flow of cells under the impact of the laser beam, traverses the first optical element and passes out of the same by dioptre 23. Part 25 of the wall of chamber 12, positioned opposite to dioptre 23 relative to the centre of said chamber, is metallized so that is reflects the light emitted by the flow of cells towards the rear of the optical device, i.e. in a propagation direction corresponding to a displacement from the centre of the chamber towards the metallized part 25, at the light emission point, where it is added to the light flow emitted towrads the front of the device, i.e. with a propagation direction corresponding to a displacement from the centre of the chamber towards dioptre 23. This leads to an increase in the collection efficiency of the optical device. Obviously, the extent of the metallized part 25 is limited so that it does not encounter the laser beam, when the latter is on the point of penetrating chamber 12.

The second optical element 10 is defined by a first concave spherical dioptre 26 and by a second convex spherical dioptre 27 allowing a common axis of symmetry. The second optical element 10 is positioned in such a way that this common symmetry axis coincides with the optical axis 24 and the concave dioptre 26 faces dioptre 23.

To prevent spherical aberrations of the optical elements 9, 10, the latter are produced by using properties of the Weierstrass points, the centre 11 of chamber 12 constituting the first Weierstrass point of dioptre 23 and the second Weierstrass point W of said dioptre 23 constitues both the centre of the first dioptre 26 and the first Weierstrass point of the second dioptre 27. The second Weierstrass point of said second dioptre 27 is designated $W_2$ in FIG. 3. In the latter, it is possible to see that the successive dioptres progressively move the image away from the point of the flow of cells which has emitted the light, so that the aperture of the emergent beams is progressively reduced. Thus, it is possible to add to the two optical elements 9 and 10, a conventional collection lens 28 positioned facing dioptre 27, in the order to transform the light beam emitted by the flow of cells and leaving the second element 20 by the second dioptre 27, into a parallel light beam 29 with a minimum spherical aberration. The collection lens 28 e.g. consists of a so-called "better form" lens, or a corrected Fresnel lens (which has no spherical aberration and a large aperture), or by an aspherical lens.

The thus obtained optical device makes it possible to obtain a collection efficiency of approximately 18%, whereas the efficiency of a lens with a diameter of 2 cm and positioned 2 cm from the emission point is only roughly 5%.

A light reflector 30, e.g. constituted by a toroidal mirror is appropriately positioned facing the second dioptre 27, in order to trap that part 31 of the beam of laser 14 which is transmitted by the flow of cells and a part 32 of the light scattered by this flow in accordance with small angles and transform the same into parallel beams on the trajectory of which is arranged a detection assembly 33.

For the performance of a small angle diffusion method, this detection assembly 33 comprises a mask 34 for absorbing beam 31 or the direct beam, whilst only permitting the passage of light beam 32, together with a photodetector 35 (e.g. a silicon photodetector) on which the light beam 32 is focused via a lens 36. Between the latter and mask 34, it is possible to place an iris diaphragm 37 for adjusting the value of the maximum angle which it is wished to take into consideration for the scattering. Photodetector 35 is obviously connected to means for processing the signals which it emits. The said processing means can be incorporated into electronic means 17.

For performing the cast shadow method, a fraction of the laser light sampled level with mask 34 by an optical fibre, a mirror or any other means is analyzed by a silicon photodetector 38, the signals emitted by this photodetector 38 being processed in appropriate means 39.

For carrying out fluorescence studies of the appropriately marked flow of cells, an optical assembly 40 (FIG. 4) for bringing about convergence of the parallel beam 29 from collective lens 28 is positioned following the latter. This optical assembly comprises e.g. a planoconvex convergent lens 41, whose convex face is turned towards the collective lens 28 and whereof the optical axis coincides with optical axis 24, as well as a planoconvex divergent lens 42, whose planar face is turned towards the planoconvex lens 41 and whose optical axis coincides with said optical axis 24. Such an optical assemlby makes it possible to obtain an adequate magnification, whilst only occupying a reduced volume.

In the case of a fluorescence study, only involving a laser and in the case where there are two fluorescence wavelengths, a dichroic mirror 43 is positioned on the path of the light beam emerging from the optical assembly 40, between the latter and the convergence zone and this mirror only permits the passage of the light corresponding to one of the two wavelengths, whilst reflecting the light corresponding to the other wavelength. This leads to two convergence zones 44, 45, respectively corresponding to the two wavelengths and said zones are defined by diaphragms 46, 47, which only permit the passage of the light from the interaction point between laser beam and the flow of cells. The wavelength selection is completed by optical fibres $F_1$, $F_1$ respectively positioned at the inlet of diaphragms 46, 47. Two photodetection means 48, 49 are respectively positioned at the end of diaphragms 46, 47 for collecting the light with an appropriate wavelength. Such photodetection means 48, 49 are connected to electronic means 17 for supplying the latter with signals permitting the sorting of the cells.

For carrying out a large angle diffusion study, a dichroic filter 50 (FIG. 4) is positioned at 45° on the optical axis 24, facing the outlet face of divergent lens 42. This filter only reflects light, whose wavelength is equal to that of the laser beam for exciting the flow of cells. A slit mask 51 is positioned following the dichroic filter 50 and, by its position, makes it possible to analyze the light scattered in angles between 0° and the maximum aperture of the optical device 8, said aperture being approximately 95°. The width of the slit defines the angular aperture $\Delta\alpha$ of the analysis. Appropriate photodetection means 55 are positioned following the analysis slit 51.

Thus, on taking account of the reflecting part 25 of chamber 12 (FIGS. 2 and 3), for a given position of the analysis slit, the sum of two scattered light flows respectively corresponding to angles $\alpha$ and $\pi+\alpha$ are measured. It is possible to separately analyze these two flows by means of a cylindrical lens 52 (FIGS. 5a and 5b), which islocated at the end of lens 42 and whereof the optical axis coincides with optical axis 24, whilst positioning laser 14 (FIG. 3) in such a way that the laser beam encounters the flow of cells at a point differeing from the centre of chamber 12. Under these conditions, the metallized part of the said chamber forms a symmetrical image 53 of the interaction point 54 between the laser beam and the flow of cells and the cylindrical lens 52 forms two parallel layers, one corresponding to the forwards emission, the other corresponding to the image formed from the rearwardly scattered light and reflected in the opposite direction by the metallized part 25. It is then possible to separately analyze on the one hand a light flux diffused between approximately 0° and 95° and on the other hand a light flux scattered between approximately 90° and 160°. These two analyses are carried out by means of the slit 51, which is displaced perpendicular to the optical axis 24 for positioning it facing the chosen flux. Obviously, following the analysis slit are positioned appropriate photodetection means 55. In place of a single slit, it would also be possible to use two slits, which would be followed by photodetection means and which would make it possible to simultaneously analyze the two diffused flows or fluxes.

As stated hereinbefore, the optical device according to the invention equipped with the optical assembly 40, makes it possible to re-form the image of the interaction point between a laser beam and the flow of cells. This is particularly important in the case where it is wished to study the fluorescence of the appropriately marked cells by using a first laser 56 and a second laser 57 (FIG. 4).

The cells are marked by fluorochromes A and B, which are respectively excited by wavelengths $\lambda_1$ and $\lambda_2$ and which then re-emit respective wavelength bands $o\lambda_3$ and $\Delta\lambda_4$ generally containing $\lambda_2$, hence the impossibility of isolating the fluorescence $\Delta\lambda_3$ from the parasitic laser light $\lambda_2$. Apart from chromatic filtering, a geometrical separation is then carried out.

Figure 4:
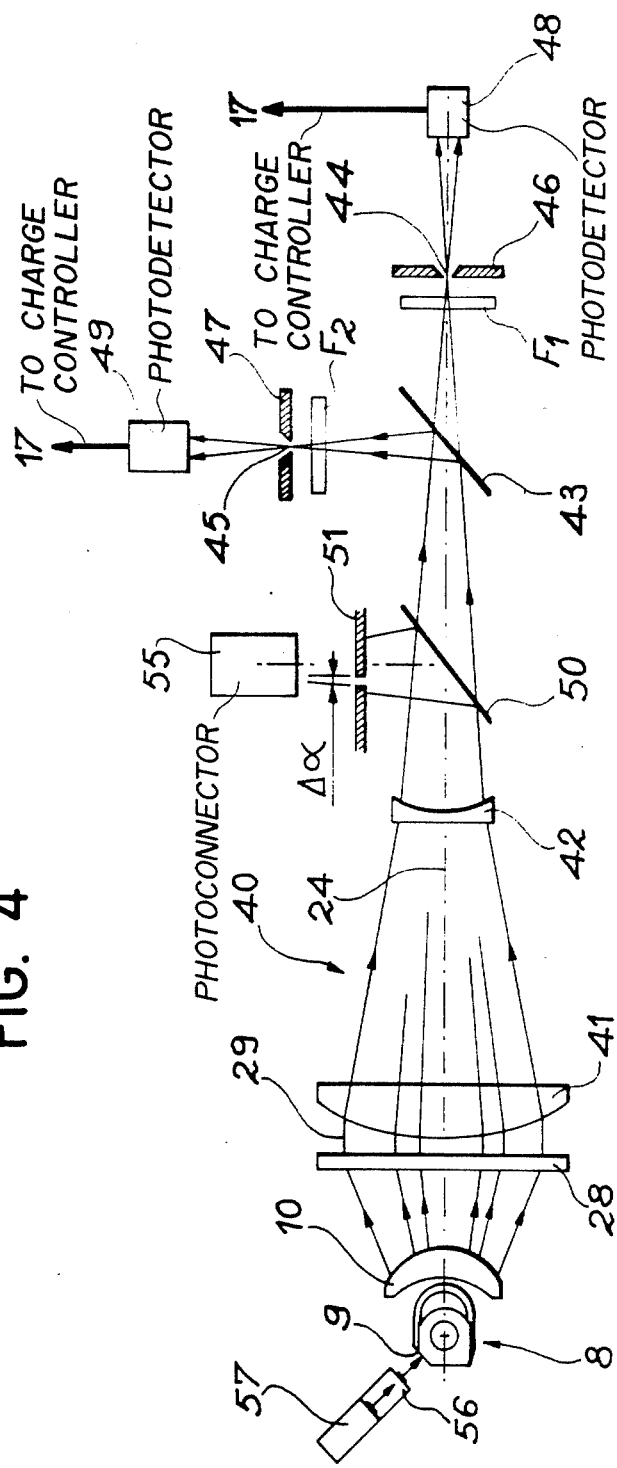
FIG. 4 a diagrammatic view of an optical assembly positioned following said device and more particularly making it possible to study the fluorescence of the biological cells.

Thus, for this purpose, the basic arrangement used is substantially identical to that used for the single laser operation (FIG. 4). The first laser is chosen to emit at wavelength $\lambda_1$ and centered in chamber 12 on optical axis 24, so that its beam is focused onto the flow of cells. The second laser emits at wavelength $\lambda_2$ and at heightwise displaced with respect to the first laser, so that the emission point resulting from the impact of the beam from the second laser on the flow of cells is heightwise displaced with respect to the emission point resulting from the impact of the beam from the first laser on the flow of cells. Bearing in mind the metallized part 25, there is an image point of the emission point corresponding to the second laser, said image points symmetrical of said emission point with respect to the chamber centre.

The optical system comprising the first element 9, the second element 10, as well as lenses 28, 41 and 42 reforms the magnified image of the three aforementioned points, in the vicinity of the photodetection means 48, 49 (dichroic mirror 43 being provided to reflect $\lambda_2$ and band $W\Delta\lambda_3$ and for transmitting band $\Delta\lambda_4$).

Diaphragms 47, 46 are replaced by masks, which only permit the arrival of the image corresponding to the emission of fluorochrome A (single point), on photodetection means 49 and the double image corresponding to the emission of fluorochrome B on photodetection means 48. It is still possible to carry out complementary optical filtering operations using filters $F_1$ and $F_2$.

Figure 6:
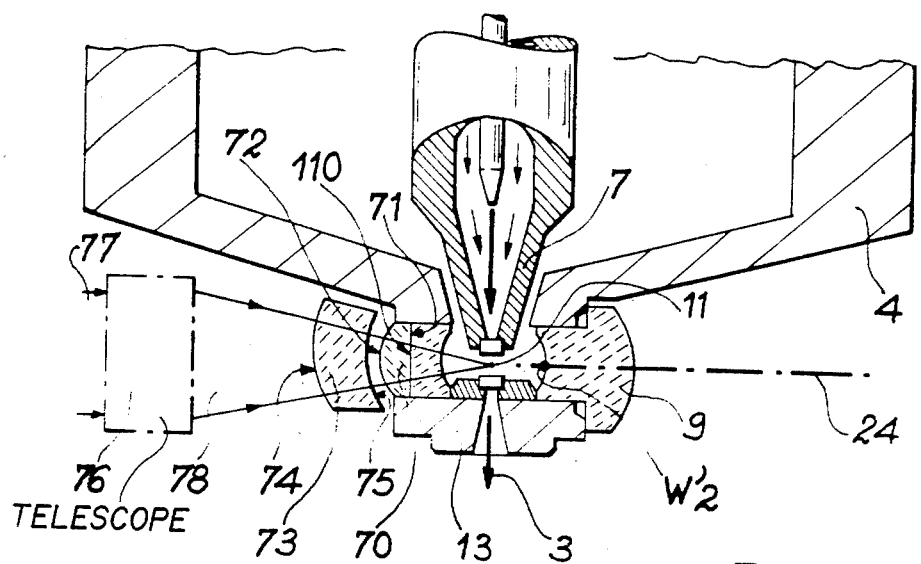
FIG. 6 a diagrammatic view of a special embodiment of the cytoflurimeter according to the invention making it possible to perform profile measurements of the cells.

For performing profile measurements on the flow of cells, i.e. for analyzing the cells portionwise, it is appropriate to illuminate this flow of cells by a light layer, which has a limited thickness compared with the length of the cells. In this case, a single lens 16 cannot be used as a result of its excessive spherical aberration compared with the size of the cells (approximately 10 microns). Moreover, an objective can no longer be used as a result of its excessive overall dimensions. Use is then made (FIG. 6) of an assembly constituted by a first lens 70 confined by a planar face 71 and by a convex spherical dioptre 72, the planar face 71 being placed against a flat 110 made on the outer face of the first optical element 9, as well as a second lens 73 defined by a convex spherical dioptre 74 and by a concave spherical dioptre 75 located facing convex dioptre 72 of first lens 70. Lenses 70 and 73 use properties of Wierstrass points to ensure a reduction of the final aperture of the beams without introducing a spherical aberration. In other words, the first Weierstrass point of the convex dioptre 72 coincides with the centre 11 of chamber 12, whilst the second Weierstrass point $W'_2$ of convex dioptre 72 constitutes both the centre of concave dioptre 75 and the first Weierstrass point of convex dioptre 74.

A telescope 76 which can be placed outside the arrangement constituted by support 4, provided with optical device 8 and lenses 70, 73 serves to transform the excitation laser beam 77 into a convergent beam 78 providing a maximum converage of the aperture of optical assembly 73, 70. This beam 78 is then focused centre 11 of chamber 12 by two lenses 70, 73. The resolution of these two lenses 70, 73 can be less than 0.8 micron for an excitation wavelength of 488 nm and approximately equal to 0.6 microns in the ultraviolet range.

Figure 7:
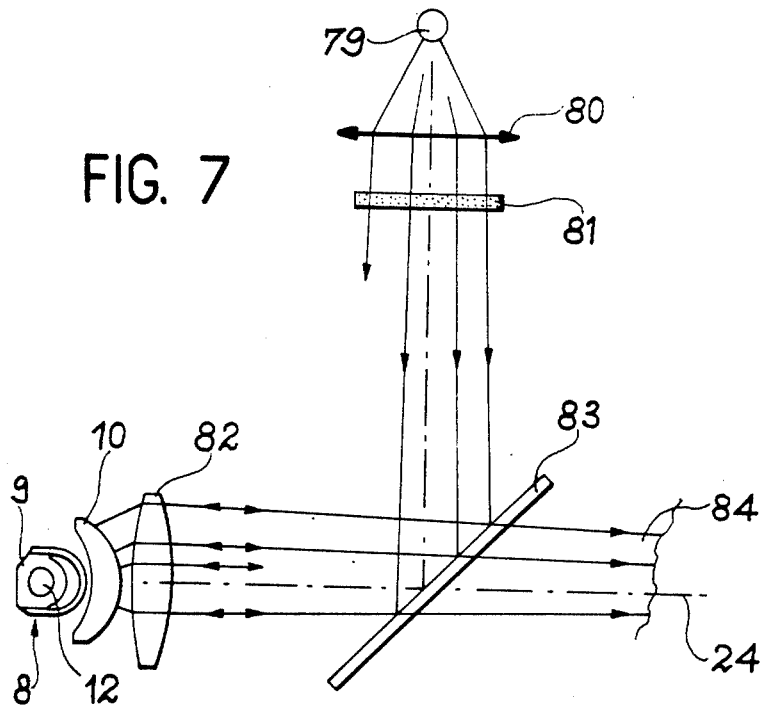
FIG. 7 a diagrammatic view of another special embodiment, not using one or more lasers, but instead an incoherent light source, whose light is injected by the outlet face of the optical device equipping the cytofluorimeter.

The aforementioned cytofluorimeter permits the performance of a large number of analysis methods, provided that appropriate means are added thereto as indicated hereinbefore. It is also possible to produce a less expensive cytofluorimeter, whose functions are specific and of a limited number. For this purpose, the laser or lasers of the cytofluorimeter are replaced by an appropriately positioned incoherent light source and e.g. constituted by a mercury vapour lamp 79 (FIG. 7). The optical device 8 accoding to the invention is perfectly adatped to a use with such a lamp, the cytofluorimeter still permitting the performance of electrical measurements of the COULTER type.

The mercury vapour lamp 79 is followed by a collection optics 80, itself followed by a filter 81 for isolating a line in the mercury emission spectrum. Lens 28 (FIG. 3), e.g. constituted by a Fresnel lens is in this case replaced by a conventional lens 82 able to transmit ultraviolet light. A dichroic lens 83 is positioned at 45° of the optical axis 24 facing lens 82 and opposite to the second element 10 with respect to said lens 82. Lamp 79, followed by lens 80 and filter 81, is positioned insuch a way that it transmits light onto dichroic mirror 83. The latter is chosen in such a way as to reflect the light emitted by lamp 79 and transmits the fluorescence light which the appropriately marked biological cells are able to emit by interaction with the light emitted by lamp 79. The light emitted by lamp 79 thus enters chamber 12 after successively traversing lens 82, second element 10 and first element 9. This light interacts with the flow of cells emitting the fluorescence light. The latter then successively passes through the first element 9, the second element 10, lens 82 and dichoric mirror 83. It is then possible to carry out fluorescence measurements on the light beam 84 emerging from dichroic mirror 83. The sorting of the cells, carried out on the basis of an analysis of said beam 84, is still possible.

Obviously, in a variant, the mercury vapour lamp could be replaced by a laser.

What is claimed is:

1. An optical device permitting at least one of the two following operations, namely
   (a) the luminous excitation of an axial flow of material to be analyzed, said flow being directed along an axis and being able to emit light when said flow receives some light and
   (b) the collection of light emitted by said flow,
   said device comprising a first optical element and an analysis chamber which chamber has a spherical shape, is formed within the first optical element and has a symmetry centre, said chamber being open at two diametrically opposite ends,
   the first optical element having an inner concave spherical dioptre, an outer convex spherical dioptre, and an axis of symmetry passing through the symmetry centre of the chamber and
   the first optical element being positioned in such a way that the axis of the material flow passes through the two ends and the centre of the chamber,
   said optical device also comprising a second optical element having an inner concave dioptre, an outer convex dioptre and an axis of symmetry, said second optical element positioned in such a way that the inner dioptre of the second optical element faces the outer dioptre of the first optical element, and that the symmetry axis of the second optical element coincides with the symmetry axis of the first optical element.

2. A device according to claim 1, wherein the analysis chamber has an optically reflecting wall positioned opposite the outer dioptre of the first optical element with respect to the chamber centre.

3. A device according to claim 1, wherein the outer dioptre of the first optical element has at least a first and a second Weierstrass point and wherein said first Weierstrass point coincides with the center of the analysis chamber.

4. A device according to claim 1, wherein the two dioptres of the second optical element have a common symmetry axis, which is the same as the symmetry axis of the second optical element.

5. A device according to claim 3, wherein the second Weierstrass point of the outer dioptre of the first optical element constitutes both the centre of the first dioptre of the second optical element and a first Weierstrass point of the second dioptre of the second optical element.

6. A device according to claim 4, further comprising a collection lens positioned facing the second dioptre of the second optical element, the optical axis of which collection lens coincides with the symmetry axis of said second dioptre,
   said collection lens being capable of forming a parallel light beam from the light which said collection lens collects from the second dioptre.

7. A cytofluorimeter comprising:
   means for forming a flow of biological cells directed along an axis, said cells being able to emit light when they receive some light;
   means for forming at least one light beam for causing luminous excitation of said cells;
   an optical device for transmitting said light beam thereby permitting said cell excitation and the collection of any light emitted by the flow of cells; and
   means for analyzing said light;
   wherein the optical device comprises a first optical element and a spherical analysis chamber formed within said first optical element and having a symmetry centre, said chamber being open at two diametrically opposite ends,
   the first optical element having an inner concave spherical dioptre, an outer convex spherical dioptre, and an axis of symmetry passing through the symmetry centre of the chamber and
   the first optical element being positioned in such a way that the axis of the material flow passes thorough the two ends and the centre of the chamber.
   said optical device also comprises a second optical element having an inner concave dioptre, an outer convex dioptre and an axis of symmetry, said second optical element positioned in such a way that the inner dioptre of the second optical element faces the outer dioptre of the first optical element, and that the symmetry axis of the second optical element coincides with the symmetry axis of the first optical element.

8. A cytofluorimeter according to claim 7, wherein at least one area of the outer dioptre of the first optical element has at least one flat portion for the entry of the light beam.

9. A cytofluorimeter according to claim 7, further comprising a light reflector for reflecting part of the light diffused and nonabsorbed by the flow of cells and for forming a parallel light beam from said diffused and non-absorbed light part.

10. A cytofluorimeter according to claim 7, further comprising:
    a collection lens positioned facing the second dioptre of the second optical element, the optical axis of which collection lens coincides with the symmetry axis of said second dioptre,
    said collection lens being capable of forming a parallel light beam from the light which said collection lens collects from the second dioptre; and
    an optical assembly for transforming the parallel light beam formed by the collection lens into a convergent light beam.

11. A cytofluorimeter according to claim 10, wherein the axis of the flow of cells is perpendicular to the axis of symmetry of the outer dioptre of the first optical element, wherein the excitation light beam is a laser beam striking the flow of cells at a point separate from the centre of the chamber, wherein the analysis chamber has an optically reflecting wall positioned opposite to the outer dioptre of the first optical element with respect to the centre of the chamber and further comprising a cylindrical lens positioned following the optical assembly and able to form tow parallel light layers from the light emerging from said assembly, at least one analysis slit for said layers and which can be displaced transversely with respect thereto and positioned following the cylindrical lens, and photodetector means positioned following the analysis slit.

12. A cytofluorimeter according to claim 10, wherein the axis of the flow fo cells is perpendicular to the axis of symmetry of the outer dioptre of the first optical element, wherein the excitation of the cells is carred out with the aid of a first laser beam and a second laser beam striking the flow of cells respectively in the centre of the analysis chamber and at a point separate from said centre and wherein the analysis chamber has an optically reflecting wall positioned opposite to the outer dioptre of the first optical element with respect to the centre of the chamber.

13. A cytofluorimeter according to claim 8, further comprising a first lens defined by a planar face and by a convex spherical dioptre, the planar face being placed against said flat portion of the first optical element, a second lens defined by a convex spherical dioptre and by a concave spherical dioptre facing the convex dioptre of the first lens and a telescope for transforming the light beam into a convergent bean with a large diameter and covering at most the convex dioptre of the second lens, wherein a first Weierstrass point of the dioptre of the first lens coincides with the centre of the analysis chamber and wherein a second Weierstrass point of this dioptre constitues both the centre of the concave dioptre of the second lens and a first Weierstrass point of the convex dioptre of said second lens.

14. A cytofluorimeter according to claim 7, wherein the light beam formation means directs said light beam into the optical device in such a way that the light beam strikes the dioptre of the first optical element of said optical device.

15. A cytofluorimeter according to claim 7, further comprising means for electrically analyzing the said cells.

16. A cytofluorimeter according to claim 7 wherein the means for forming the flow comprise a first nozzle which issues into the chamber via one of said two diametrically opposite ends, and the cytofluorimeter further comprises:

a second nozzle which issues out of the chamber via the other of said two diametrically opposite ends and is located facing said first nozzle;

means for electrically analyzing the said cells, and means for sorting the cells, said sorting means being positioned at the exit of said second nozzle.

* * * * *